(12) United States Patent
Wagner et al.

(10) Patent No.: US 7,995,827 B2
(45) Date of Patent: Aug. 9, 2011

(54) ARTEFACT ELIMINATION FOR A MEDICAL PELVIC REGISTRATION USING A TRACKED PELVIC SUPPORT KNOWN TO THE SYSTEM

(75) Inventors: Benjamin Wagner, München (DE); Timo Neubauer, Poing (DE)

(73) Assignee: BrainLAB AG, Feldkirchen (DE)

( * ) Notice: Subject to any disclaimer, the term of this patent is extended or adjusted under 35 U.S.C. 154(b) by 902 days.

(21) Appl. No.: 11/958,833

(22) Filed: Dec. 18, 2007

(65) Prior Publication Data

US 2008/0144914 A1    Jun. 19, 2008

Related U.S. Application Data

(60) Provisional application No. 60/882,766, filed on Dec. 29, 2006.

(30) Foreign Application Priority Data

Dec. 19, 2006    (EP) .................................... 06026291

(51) Int. Cl.
  *G06K 9/00*    (2006.01)
  *A61B 5/05*    (2006.01)
(52) U.S. Cl. .......................... 382/132; 382/275; 600/424
(58) Field of Classification Search .................. 382/100, 382/134, 128, 129, 130, 131, 132, 133, 168, 382/173, 181, 232, 254–260, 274, 275, 276, 382/291, 293–299, 305, 312; 5/624; 378/20, 378/62; 600/424, 426, 407
See application file for complete search history.

(56) References Cited

U.S. PATENT DOCUMENTS

| | | | | |
|---|---|---|---|---|
| 5,442,674 A * | 8/1995 | Picard et al. ..................... | 378/20 |
| 6,311,349 B1 * | 11/2001 | Kazakia et al. .................... | 5/624 |
| 6,470,207 B1 * | 10/2002 | Simon et al. ................... | 600/426 |
| 6,493,573 B1 * | 12/2002 | Martinelli et al. ............ | 600/424 |
| 7,542,791 B2 * | 6/2009 | Mire et al. ..................... | 600/407 |
| 7,835,784 B2 * | 11/2010 | Mire et al. ..................... | 600/424 |
| 2002/0154735 A1 * | 10/2002 | Simon et al. ..................... | 378/62 |
| 2004/0199072 A1 * | 10/2004 | Sprouse et al. ............... | 600/424 |
| 2005/0076441 A1 | 4/2005 | Dominati et al. | |

FOREIGN PATENT DOCUMENTS

| | | |
|---|---|---|
| EP | 1 522 300 | 4/2005 |
| EP | 1 627 601 | 2/2006 |
| WO | 2004/017263 | 2/2004 |
| WO | 2004/089192 | 10/2004 |
| WO | 2005/084541 | 9/2005 |

* cited by examiner

*Primary Examiner* — Seyed Azarian

(74) *Attorney, Agent, or Firm* — Renner, Otto, Boisselle & Sklar, LLP

(57) ABSTRACT

A system for registering a patient's body part in a medical workspace of a medical navigation system is provided, wherein the body part is supported by at least one support device. The system includes a medical navigation system including a processor and memory, a reference device coupled to the at least one support device, a tracking device communicatively coupled to the medical navigation system and operative to determine a position of the reference device; an x-ray or fluoroscopic apparatus for capturing x-ray or fluoroscopic images of the body part; and logic stored in memory and executable by the processor. The logic includes logic that eliminates an effect of image artefacts on registration of the body part, wherein the artefacts are caused by the at least one support device.

16 Claims, 6 Drawing Sheets

ARTEFACT ELIMINATION FOR A MEDICAL PELVIC REGISTRATION USING A TRACKED PELVIC SUPPORT KNOWN TO THE SYSTEM

RELATED APPLICATION DATA

This application claims priority of U.S. Provisional Application No. 60/882,766 filed on Dec. 29, 2006, which is incorporated herein by reference in its entirety.

FIELD OF THE INVENTION

The invention relates generally to medical registration and, more particularly, to artefact elimination for medical pelvic registration using a tracked pelvic support.

BACKGROUND OF THE INVENTION

In pelvic operations, in particular in hip replacement operations, patients typically are operated on while lying on their side, wherein it may be necessary to fix the patient's pelvis such that it is immobile. This can be achieved using patient positioners that include support devices for the lower region of the patient's body. In this position, however, it is difficult to ascertain navigation information by tapping body landmarks (ASIS and pubic points) within the framework of medical navigation. This is due to the fact that these characteristic pelvic landmarks are in most cases almost inaccessible, at least in the lower region. X-ray or fluoroscopic registration are therefore often used.

Many of the conventional patient positioners use cushions or rods that are fixed to an arm system of the operating table or to similar fixed means. Such a mechanical positioner, for example, is known from U.S. Pat. No. 6,311,349.

In addition to mechanical positioners, there are also positioners that include navigation reference means for medical navigation; such a positioner, for example, is known from WO 2004/089 192 A2. The reference means can be used to indirectly localize the ASIS and pubic points and, therefore, to register the front pelvic plane.

A problem with existing positioning means is seen when fluoroscopic images are recorded. It is within the nature of the positioning means that at least a part of their support devices lie in the radiation path of the fluoroscopic recording and, therefore, can create artefacts on the recording. Even if the chosen materials for the support device are permeable to x-ray radiation, shadows and edges may still be created on the images. These artefact contours superpose the anatomical structure (pelvis) and could result in a misinterpretation of the recordings. The navigation software, for example, detect anatomical structures in order to register the pelvis, and the above-mentioned shadows and edges could in this case lead to an incorrect choice of contour and, thus, to incorrect registration. In addition, it is difficult to define points in the region of the support images because the contrast such regions suffers due to the artefacts.

SUMMARY OF THE INVENTION

An artefact elimination method in accordance with the invention serves a medical pelvic registration for positionally registering a patient's pelvis that is supported by at least one support. The method can include the following steps:

the geometric data of the support can be stored in memory of a medical navigation system that is used for registration;

at least two x-ray or fluoroscopic recordings of the patient's pelvis can be produced or obtained, wherein the support is situated in the radiation path of the recording;

a position of the support and of the x-ray or fluoroscopic apparatus during the recording can be ascertained by the navigation system;

with the aid of the ascertained positional data for the support and the x-ray or fluoroscopic apparatus, the image of the support is identified in the recording;

the recording is used for registration, wherein the image elements of the identified image of the support are defined as parts of the image that are not to be used in registering.

Thus, the method in accordance with the invention can use known dimensions of the support and a known position of the support in order to disregard the support image during registration. Because it is known where the support lies and what its image will look like, it is possible to avoid registration based on the imaged support elements.

The method, with the assistance of medical navigation, enables a patient to be laterally positioned during a pelvic operation and the anatomical pelvic landmarks to be correctly registered, without the registration being influenced by the support. The problem of support artefacts in the recording no longer occurs, because the support can be tracked (e.g., using the reference means in conjunction with the support's geometric data (dimensions, internal structure, etc.), which can be stored in a database of the navigation software). By tracking the support, the image features pertaining to the support can be recognized. More specifically, support artefacts in the image can be calculated and, based on these calculations, artefacts due to the support can be disregarded during registration.

The image elements of the identified image of the support can be subtracted from the recording, which can be achieved by suitable graphics software and graphics hardware. The pelvic points and pelvic contours that are actually to be used remain in the image for registration.

In principle, all the support elements imaged in the recording can be "calculated out" of the recording. On the other hand, it is often sufficient to identify the imaged contours of the support in the recording and to define them as parts which are not to be used.

When identifying the support image, it is possible to use grey values of the support image elements as an identification aid, in particular known or substantially known grey values that are usually generated by the materials of the support. When identifying the support image, it is advantageous if distance ratios of the support elements (e.g., outer contours, inner contours, corners) are used, i.e., known distances between such elements and determined points or parts of the support which are easily identified in the recording. Such starting points for calculating the support image, for example, can be support elements that can be clearly imaged. However, it is also possible to attach additional markers in or to the support and to use these additional markers as identification aids and/or starting points for determining distances. Imaginary lines or planes also can be used as such starting points or identification aids. For example, an imaginary connecting line between specific markers that can be clearly imaged can be used as an identification aid and/or starting point.

An artefact elimination system in accordance with the invention serves to eliminate artefacts in x-ray or fluoroscopic recordings that are used in a medical pelvic registration method for positionally registering a patient's pelvis supported by at least one support. The system includes:
- a medical navigation system;
- a tracking device operative to determine a position of navigation reference means;
- an x-ray or fluoroscopic apparatus; and
- a navigation reference array positionally assigned to the support.

The system is characterized by:
- a medical navigation system; and by
- logic in the navigation system which, on the basis of the information on the geometric data of the support, disregards the image of the support in an x-ray or fluoroscopic recording during registration.

Preferably, the support already consists of a material that is permeable to x-rays, and in an embodiment, one or more markers made of a material that is substantially impermeable to x-ray radiation is/are arranged on the support at a known distance from the support elements. These markers serve as identification aids or "starting points" for calculating the position of the support image.

It is also possible within the framework of the invention for the positioner itself to be configured such that, although it holds the pelvis in the region between the ASIS and pubic landmarks, it allows these landmarks to be tapped using a navigation pointer, so as to digitize these points for registrations. This can be achieved by shaping the support so as to allow free access to these landmark points.

Also provided herein are a program which, when it is running on a computer or is loaded on a computer, causes the computer to perform one of the methods described herein, and to a computer program storage medium which comprises such a program.

BRIEF DESCRIPTION OF THE DRAWINGS

The forgoing and other features of the invention are hereinafter discussed with reference to the drawings.

DETAILED DESCRIPTION

Figure 1:
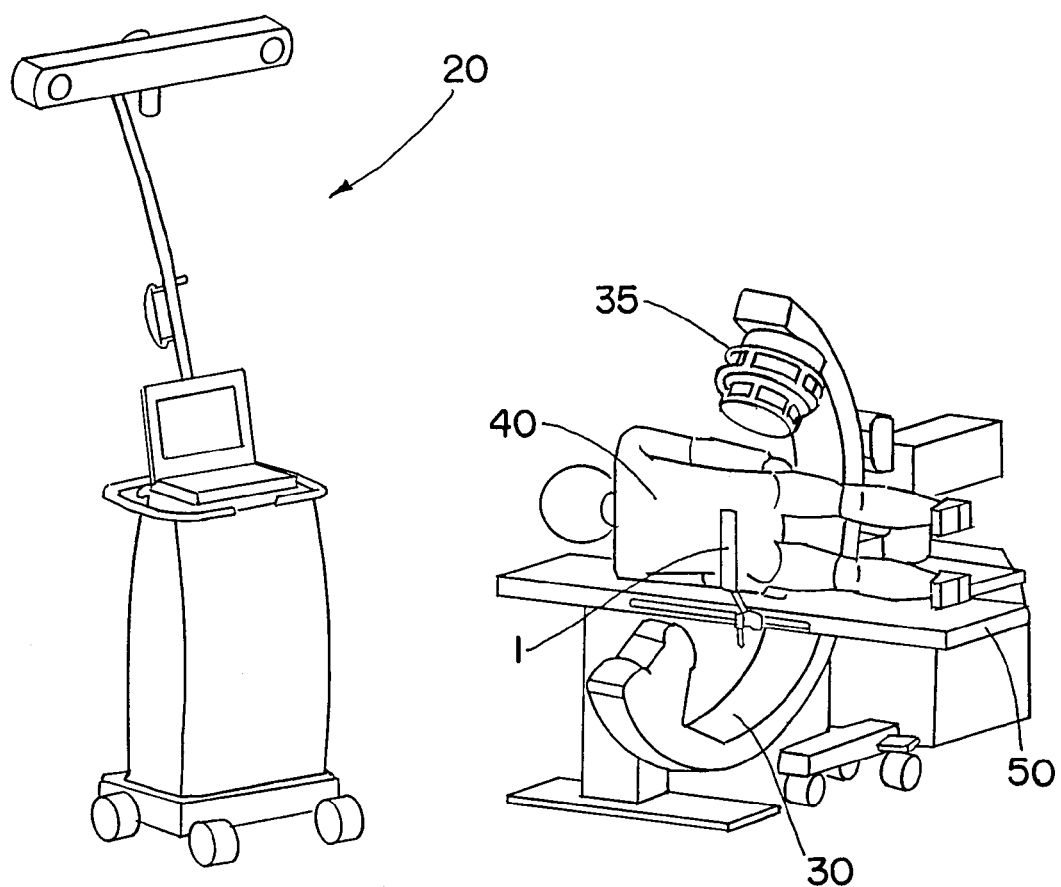
FIG. 1 is an exemplary operating theatre set-up for performing a pelvic registration, wherein the set-up can be used in conjunction with the present invention.

FIG. 1 provides a general overview of an application setting in which a support device in accordance with the invention may be used. More specifically, FIG. 1 shows a patient 40 lying laterally on the patient table 50. The patient 40 is supported or fixed, and a front support of a patient positioner used for this purpose is indicated by the reference sign 1. In order to produce x-ray images, in particular in order to fluoroscopically assist pelvic registration, a C-arm fluoroscope 30 is arranged on the patient table 50 and comprises a so-called registration kit 35 at its radiation source. With the aid of the registration kit 35, which comprises reference means, it is possible to ascertain the position of the C-arm 30 by using a medical navigation system 20, which is shown to the left of the patient table. The position of the fluoroscopic recording and the recording angle can thus be spatially determined.

Figure 2:
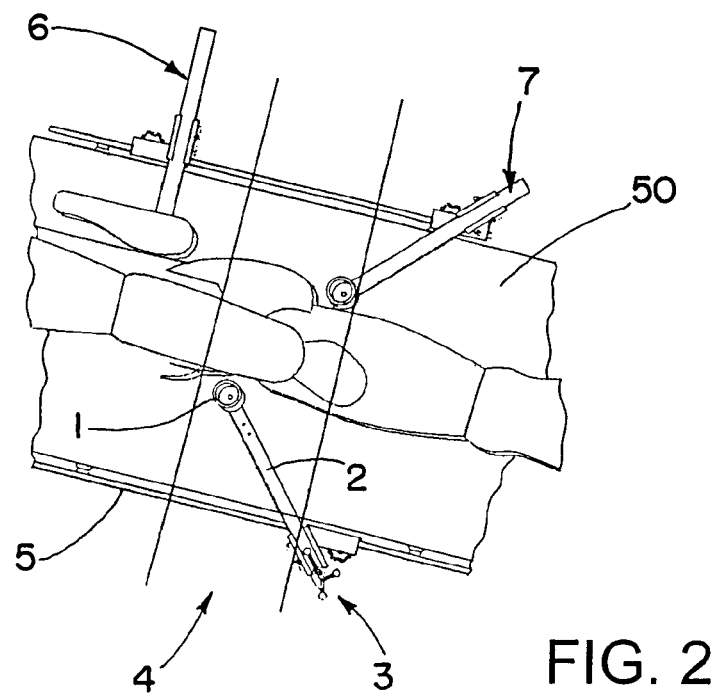
FIG. 2 is an exemplary view from above a supported patient.

A holding device for the support 1 also bears a navigation reference. This navigation reference is not visible in FIG. 1 due to the scale, but is shown in FIGS. 2 to 5. FIG. 2 shows a view from above onto the patient 40 lying on the patient table 50, supported in the pelvic region by three support devices. The two rear support devices are indicated as a whole by the reference signs 6 and 7; the front support means is indicated in more detail, and its components also can be seen in FIGS. 3 to 5. The front support means comprises the rod-like support 1 and a holding arm 2, on the other end of which a reference means 3 (e.g., a reference array) is attached. This reference array 3 comprises three marker spheres that can be detected by the navigation system 20 (FIG. 1), and due to the rigid positional assignment between the support 1 and the reference array 3, the exact spatial position of the support 1 is known by detecting a position of the spheres.

In FIG. 2, a radiation path is indicated by the two parallel lines bearing the reference sign 4. As can be seen, parts of the support device, namely the support 1 itself and parts of the arm and a holding device 8 (FIG. 3), are situated in front of the pelvis and in the radiation path of the fluoroscopic apparatus.

Figure 3:
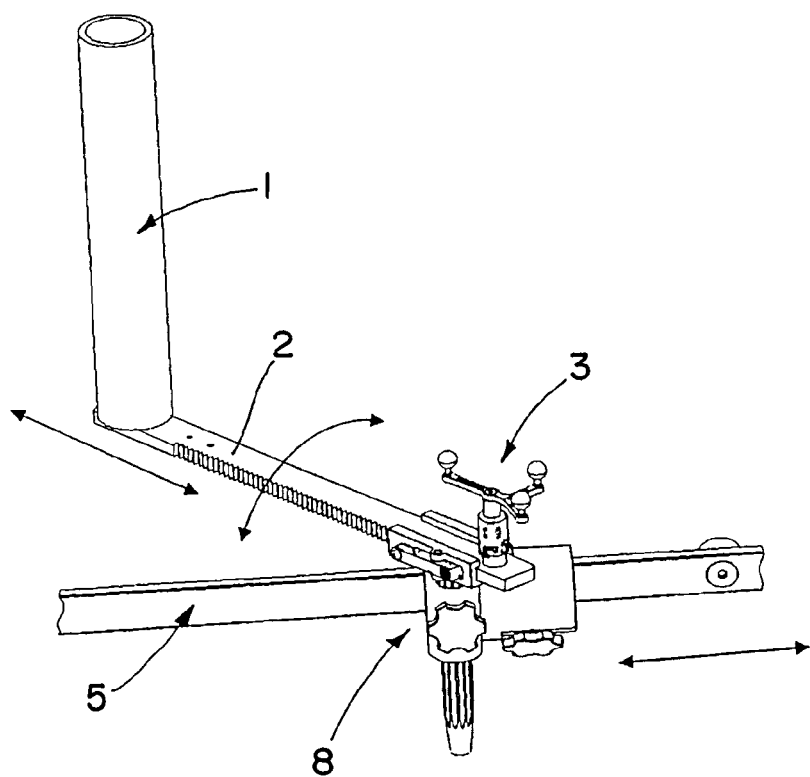
FIG. 3 is a perspective view of an exemplary patient support device.
Figure 4:
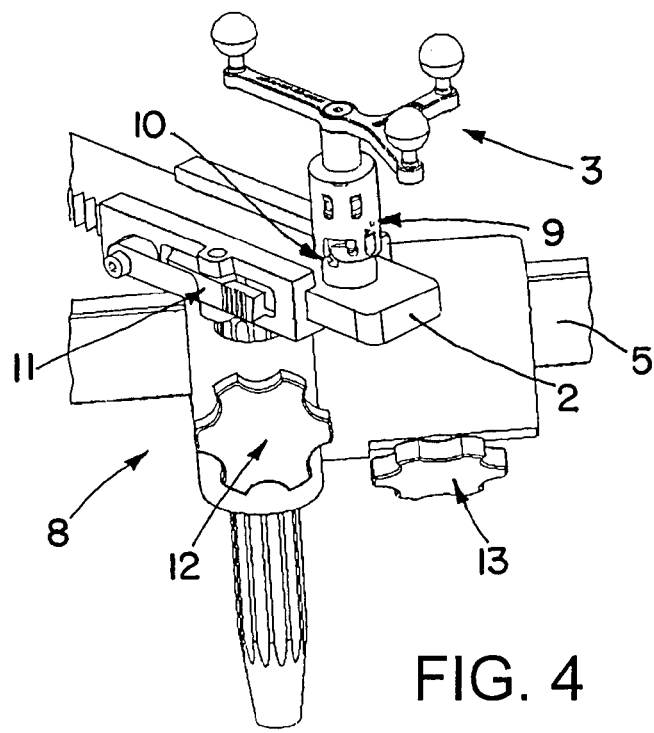
FIG. 4 is a detail view of a portion of the support device of FIG. 3.

With further reference to FIGS. 3 and 4, the holding device 8 can be movably fastened to a rail 5 that is fixed to the patient table 50. The position of the holding device 8 can be fixed along the rail 5 using a rotational quick-release lock 13. The reference sign 12 indicates a quick-release lock mechanism that fixes and/or releases the rotation and/or pivoting of the arm 2. A quick-release lock mechanism 11 allows the arm to be fixed in its sliding longitudinal guide. An adaptor 10 for the reference means can be arranged, as mentioned, almost at the rear end of the arm 2, and a quick-release lock mechanism 9 for the reference means 3 can be placed on said adaptor 10. The quick release lock mechanism 9 allows the reference means 3 to be quickly attached and removed from the adapter. With the aid of this construction, the support 1 can then be positioned at a desired point on the front of the patient's pelvis and fixed in place.

Figure 5:
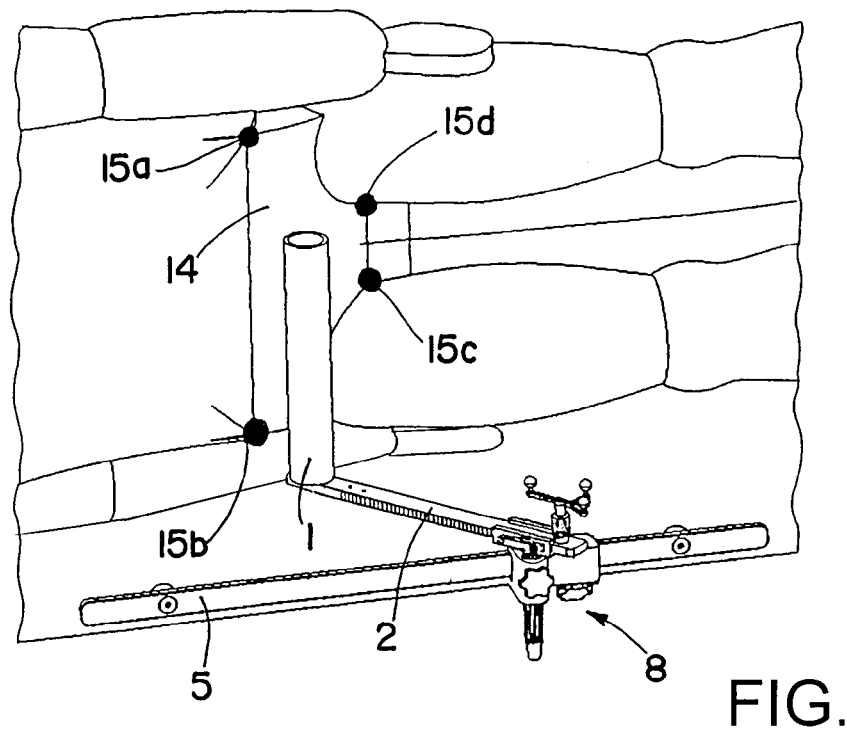
FIG. 5 is a schematic view of the exemplary patient pelvic support device.

A support 1 embodied as an elongated rod in conjunction with the various ways of moving and fixing the holding means 8 (e.g., pivoting movement of the arm, sliding movement of the arm and lateral adjustment on the rail 5) ensure that the support 1 can be freely positioned, wherein a fixed hold in the fixing position is simultaneously provided. This enables the patient to be fixed on the front side of the pelvis in such a way that the ASIS and pubic points 15a, 15b, 15c, 15d are not occluded by the support 1, but that the support comes to rest between these points as shown in FIG. 5. When the patient's pelvis is fixed, a navigation pointer then can be moved to these body landmarks and their position can be registered.

Figure 6:
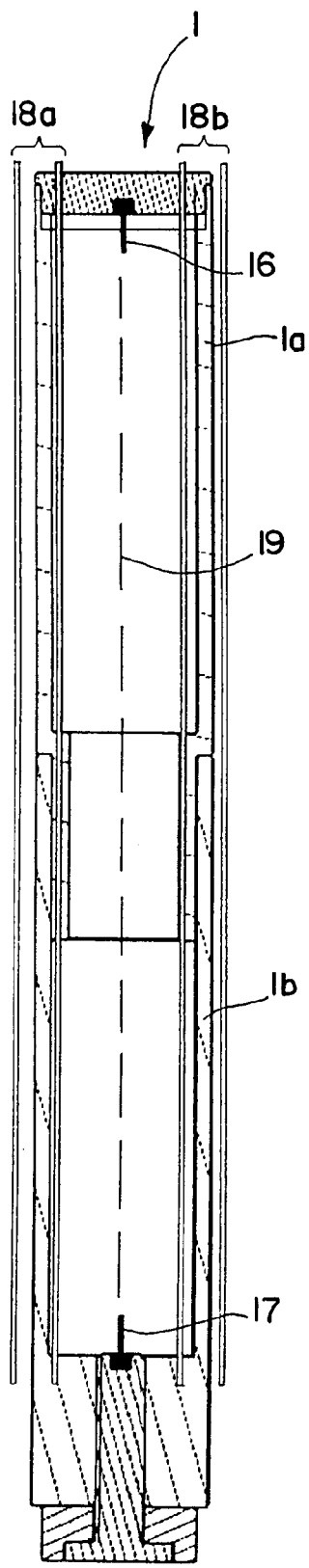
FIG. 6 is an exemplary support for use with the present invention.

The support 1 shown in a longitudinal section in FIG. 6 is particularly well suited to artefact elimination in accordance with the present invention. The support includes an upper part 1a and a lower part 1b that are plugged or coupled together along a mid-section of the respective parts. The exemplary support is tubular and substantially consists of a material that is permeable to x-ray radiation. Markers 16 and 17 can be inserted in the lid and lower insert of the support 1 and consist of a material that is impermeable to x-ray radiation. The reference signs 18a and 18b indicate regions that comprise the edge contours of the support 1. An imaginary connecting line between the markers 16 and 17 is indicated by the reference sign 19.

Using a support in accordance with FIG. 6, the method in accordance with the invention may be performed as follows. Generally, for navigation assistance, the position of the front pelvic plane is ascertained using the navigation system 20, wherein this position is determined using the ASIS and pubic points 15a to 15d. When performing fluoroscopic registration using the fluoroscopic apparatus 30 (FIG. 1), reference arrays can be fastened to the patient's pelvis and femur for this purpose. Two fluoroscopic images can be produced in the region of the pelvis, and a navigation pointer can be moved to the ASIS (anterior superior iliac spine) point on the side to be treated so as to register this point. The system then calculates the anatomical landmarks of the pelvis, specifically in the anterior pelvis plane and the mid-sagittal plane, on the basis of the imaged edges of the pelvis on the fluoroscopic recording.

Despite the radiolucency of the support 1, the support can create artefacts in the image in the region of pelvic edges, and these artefacts can distort the image edges and/or contours, leading to registration errors. More specifically, if the fluoroscopic image is taken with the support 1 and the additional markers 16 and 17 in the radiation path, the image of the support causes shadows and edges on the image. Because the support 1 consists of a different material or of different materials, different grey values are created on the recording. Since the markers 16 and 17 are manufactured from a material which is impermeable to x-rays (e.g., steel), they appear almost black on the recording. The edges of the support appear in a light grey coloration.

The black images of the markers 16 and 17 on the recording are detected by a hardware and software provided in accordance with the invention (for example in the navigation system), and a search can be conducted for specific grey values at a predetermined distance from the markers 16, 17 and/or from the imaginary connecting line 19. These specific distances, for example, are indicated by the regions 18a and 18b in FIG. 6, and comprise the edges of the support image. These edges, with their specific grey values, are then disregarded when subsequently detecting the anatomical structures of the pelvis, such that it is ensured that the pelvic contours used for registration do actually describe imaged pelvic lines. Registration then can be correctly performed using the artefact elimination in accordance with the invention.

Figure 7:
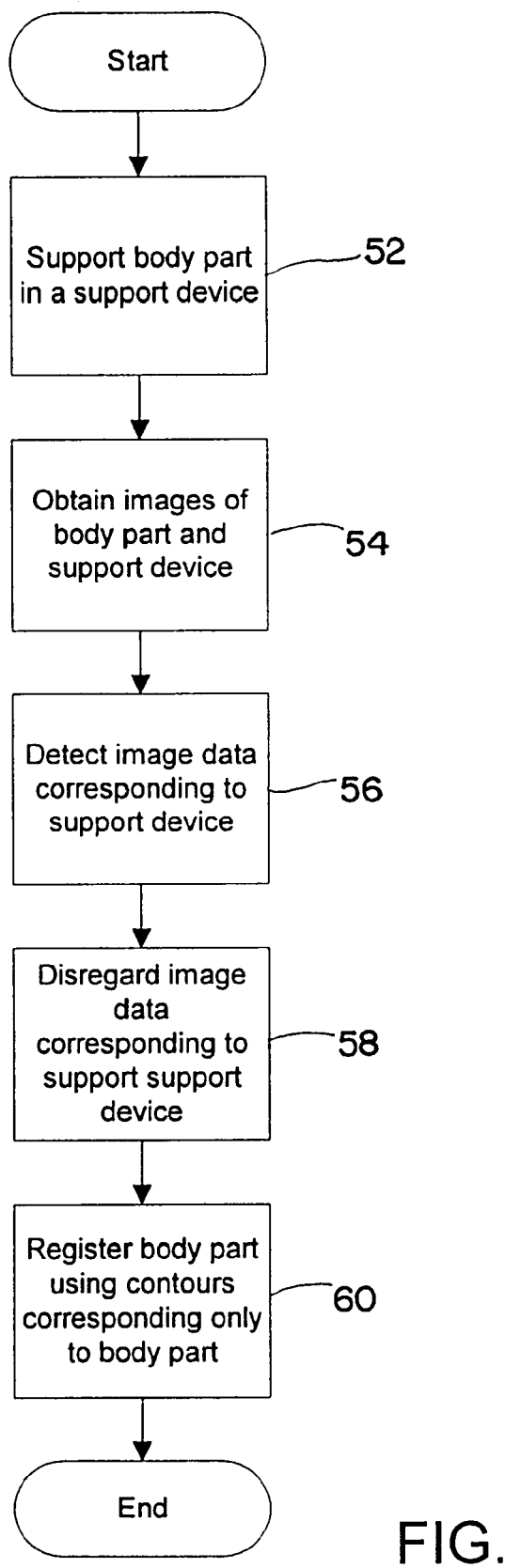
FIG. 7 is a flow chart illustrating exemplary steps of a method for removing image artefacts in accordance with the invention.

FIG. 7 is a flow chart illustrating exemplary steps for removing image artefacts in accordance with the invention. Beginning at block 52, a body part is placed in a support device in preparation for imaging. The support device, for example, may be a pelvic support device as shown in FIGS. 2-6. The support device maintains the body part in a fixed orientation relative to the imaging device such that images of the body part can be obtained. Next at block 54, images of the body part are produced or otherwise captured, wherein at least a part of the support device is also imaged (e.g., part of the support device is within a radiation path of the imaging system). At block 56, image data corresponding to the support device is detected within the captured image. Detection of the support device image data can be accomplished, for example, based on known locations of the support device relative to the imaging apparatus (e.g., the support device and imaging apparatus are tracked), a known geometry of the support device, or grey values in the image data that are typically produced by material of the support device. Next at block 58, image data determined as being part of the support device is removed, or compensations for such data can be made. For example, in determining a contour of the body part, image data determined to be part of the support device can be removed (e.g., subtracted from the image data) from the image data, thereby leaving only data corresponding to the body part. Once compensations have been made to take into account image data of the support device, then at block 60 the body part can be registered.

Figure 8:
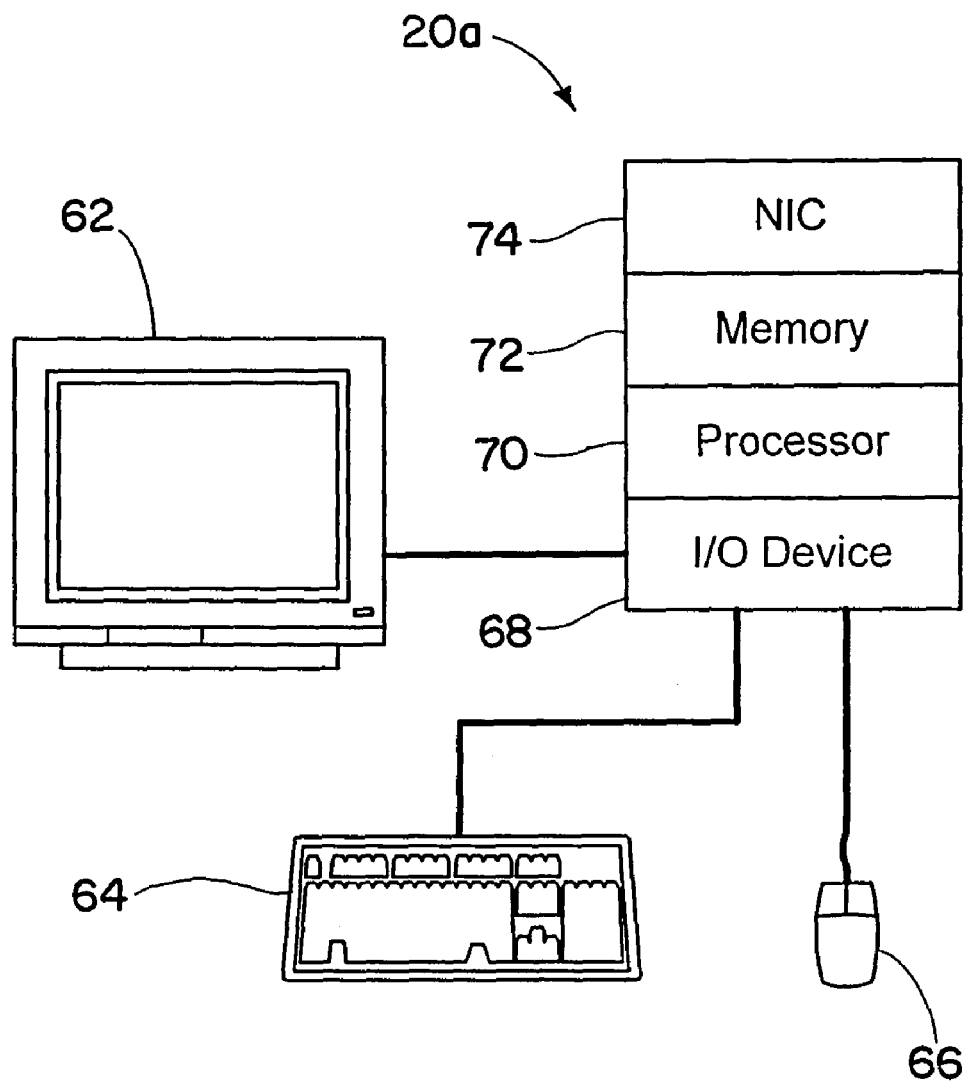
FIG. 8 is a block diagram of a computer system that can be used to implement the method in accordance with the invention.

Moving now to FIG. 8 there is shown a block diagram of an exemplary computer 20a that may be used to implement the method described herein. The computer 20a may include a display 62 for viewing system information, and a keyboard 64 and pointing device 66 for data entry, screen navigation, etc. A computer mouse or other device that points to or otherwise identifies a location, action, etc., e.g., by a point and click method or some other method, are examples of a pointing device 66. Alternatively, a touch screen (not shown) may be used in place of the keyboard 64 and pointing device 66. The display 62, keyboard 64 and mouse 66 communicate with a processor via an input/output device 68, such as a video card and/or serial port (e.g., a USB port or the like).

A processor 70, such as an AMD Athlon 64® processor or an Intel Pentium IV® processor, combined with a memory 72 execute programs to perform various functions, such as data entry, numerical calculations, screen display, system setup, etc. The memory 72 may comprise several devices, including volatile and non-volatile memory components. Accordingly, the memory 72 may include, for example, random access memory (RAM), read-only memory (ROM), hard disks, floppy disks, optical disks (e.g., CDs and DVDs), tapes, flash devices and/or other memory components, plus associated drives, players and/or readers for the memory devices. The processor 70 and the memory 72 are coupled using a local interface (not shown). The local interface may be, for example, a data bus with accompanying control bus, a network, or other subsystem.

The memory may form part of a storage medium for storing information, such as application data, screen information, programs, etc., part of which may be in the form of a database. The storage medium may be a hard drive, for example, or any other storage means that can retain data, including other magnetic and/or optical storage devices. A network interface card (NIC) 74 allows the computer 20a to communicate with other devices.

A person having ordinary skill in the art of computer programming and applications of programming for computer systems would be able in view of the description provided herein to program a computer system 20a to operate and to carry out the functions described herein. Accordingly, details as to the specific programming code have been omitted for the sake of brevity. Also, while software in the memory 72 or in some other memory of the computer and/or server may be used to allow the system to carry out the functions and features described herein in accordance with the preferred embodiment of the invention, such functions and features also could be carried out via dedicated hardware, firmware, software, or combinations thereof, without departing from the scope of the invention.

Computer program elements of the invention may be embodied in hardware and/or in software (including firmware, resident software, micro-code, etc.). The invention may take the form of a computer program product, which can be embodied by a computer-usable or computer-readable storage medium having computer-usable or computer-readable program instructions, "code" or a "computer program" embodied in the medium for use by or in connection with the instruction execution system. In the context of this document, a computer-usable or computer-readable medium may be any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium such as the Internet. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner. The computer program product and any software and hardware described herein form the various means for carrying out the functions of the invention in the example embodiments.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A method for registering a patient's body part in a medical workspace of a medical navigation system, wherein said body part is supported by at least one support device, comprising:
    obtaining at least two x-ray or fluoroscopic recordings of the body part, wherein the at least one support device is situated in a radiation path of an x-ray or fluoroscopic recording apparatus during recordation of the at least two x-ray or fluoroscopic recordings;
    using the medical navigation system to ascertain a position of the at least one support device and of the x-ray or fluoroscopic apparatus during recordation of the at least two x-ray or fluoroscopic recordings;
    using the ascertained position of the at least one support device and the x-ray or fluoroscopic apparatus to identify an image of the at least one support device in the at least two x-ray or fluoroscopic recordings;
    using the at least two recordings to register the body part in the medical workspace, wherein image data corresponding to the image of the at least one support device are not used to register the body part.

2. The method according to claim 1, wherein ascertaining a position of the at least one support device includes:
    attaching a reference device to the at least one support device; and
    using the navigation system to track a position of the reference device.

3. The method according to claim 1, wherein ascertaining a position of the at least one support device includes using known geometric data of the at least one support device to ascertain said position.

4. The method according to claim 3, wherein using known geometric data includes retrieving geometric data of the at least one support device from memory of the medical navigation system.

5. The method according to claim 1, wherein using the at least two recordings to register the body part includes subtracting the image data of the of the at least one support device from the at least two recordings.

6. The method according to claim 1, wherein image data corresponding to the image of the at least one support device includes image contours of the at least one support device.

7. The method according to claim 1, wherein identifying the image of the at least one support device includes using known grey values generated in the at least two recordings as an aid for identifying the image of the at least one support device.

8. The method according to claim 1, wherein identifying the image of the at least one support device includes using known distances between support elements of the at least one support device as an identification aid.

9. The method according to claim 1, wherein identifying the image of the at least one support device includes using known distances between support elements of the at least one support device and markers attached to the support device as identification aids.

10. The method according to claim 1, wherein identifying the image of the at least one support device includes using known distances between support elements of the at least one support device and connecting lines of specific markers in or on the support as identification aids.

11. A system for registering a patient's body part in a medical workspace of a medical navigation system, wherein said body part is supported by at least one support device, comprising:
    a medical navigation system including a processor and memory;
    a reference device coupled to said at least one support device;
    a tracking device communicatively coupled to said medical navigation system and operative to determine a position of said reference device;
    an x-ray or fluoroscopic apparatus for capturing x-ray or fluoroscopic images of the body part; and
    logic stored in said memory and executable by said processor, said logic including logic that eliminates an effect of image artefacts on registration of the body part, wherein said artefacts are caused by said at least one support device.

12. The system according to claim 11, wherein said logic that eliminates the effect of image artefacts includes:
    logic that ascertains a position of the at least one support device and of the x-ray or fluoroscopic apparatus during image capture;
    logic that uses the ascertained position of the at least one support device and of the x-ray or fluoroscopic apparatus to identify an image of the at least one support device in the captured image; and
    logic that prior to registration removes the image data corresponding to the at least one support device from the captured image data.

13. The system according to claim 11, wherein geometric data of the at least one support device are stored in said memory.

14. The system according to claim 11, wherein the at least one support device consists of a material that is permeable to x-ray radiation.

15. The system according to claim 12, further comprising at least one marker arranged on the at least one support device at known locations relative to support elements of the at least one support device, said at least one marker comprising a material that is substantially impermeable to x-ray radiation.

16. A computer program stored on a machine readable medium for registering a patient's pelvis in a medical workspace of a medical navigation system, wherein said pelvis is supported by at least one support device, comprising:

code that directs the acquisition of at least two x-ray or fluoroscopic recordings of the body part, wherein the at least one support device is situated in a radiation path of an x-ray or fluoroscopic recording apparatus during recordation of the at least two x-ray or fluoroscopic recordings;

code that ascertains a position of the at least one support device and of the x-ray or fluoroscopic apparatus during recordation of the at least two x-ray or fluoroscopic recordings;

code that uses the ascertained position of the at least one support device and the x-ray or fluoroscopic apparatus to identify an image of the at least one support device in the at least two x-ray or fluoroscopic recordings;

code that uses the at least two recordings to register the body part in the medical workspace, wherein image data corresponding to the image of the at least one support device are not used to register the body part.

* * * * *